United States Patent [19]
Otto et al.

[11] Patent Number: 5,756,311
[45] Date of Patent: May 26, 1998

[54] METHOD FOR SYNTHESIZING SOLUBLE RECOMBIANT PROTEINS FROM BACTERIA CELLS

[75] Inventors: Bernd Otto, Hanover; Gero Waschutza, Meinersen; Hayssam Zakaria, Hanover, all of Germany

[73] Assignee: Fraunhofer-Gesellschaft zur Forderung der angewandten Forschung e. V., Munich, Germany

[21] Appl. No.: 798,337

[22] Filed: Feb. 10, 1997

[30] Foreign Application Priority Data

Feb. 8, 1996 [DE] Germany ............... 196 04 583.5

[51] Int. Cl.$^6$ ............... C12P 21/04; C12N 1/21; C07H 21/04
[52] U.S. Cl. ............... 435/69.51; 435/252.3; 435/252.33; 536/23.1
[58] Field of Search ............... 435/6, 69.1, 243, 435/252.3, 320.1; 536/23.1

[56] References Cited

U.S. PATENT DOCUMENTS 5,639,635   6/1997   Joly et al. ............... 435/69.7

OTHER PUBLICATIONS

E. Amann and J. Brosius, Gene 40, 1985 (pp. 183–190).
P. Pognonec et al., Nucleic Acids Research vol. 19, No. 23 (1991) p. 6650.
C. Schein, Bio/Technology vol. 7, pp. 1141–1149 (Nov. 1989).
T. Atkinson et al., World Biotech Rep., pp. 399–405 (1988).
Chemical Abstracts 109:21583b (1988) [C. Shein et al., Bio/Technology, 1988 6(3), pp. 291–294].
Copy of the First Official Action on the German Application and English Translation.
An English translation of Applicant's response.

*Primary Examiner*—David Guzo
*Assistant Examiner*—William Sandals
*Attorney, Agent, or Firm*—Greenblum & Bernstein, P.L.C.

[57] ABSTRACT

The invention relates to a method of manufacturing soluble recombinant proteins from bacteria, in which the plasmid contains the entire gene behind a promoter, this plasmid being expressed and the protein obtained being isolated and purified, in which the cell culture is raised to an OD 600 nm of 0.4 to 0.6; the cell culture is cooled over a period of 15 to 40 minutes to 20° to 26° C.; synthesis is induced by addition of 10 to 55 µM of an inductor; and the induction phase is carried out at a temperature of 20° to 26° C. over a period of 3.5 to 6.5 hours.

28 Claims, 1 Drawing Sheet

METHOD FOR SYNTHESIZING SOLUBLE RECOMBIANT PROTEINS FROM BACTERIA CELLS

CROSS REFERENCE TO RELATED APPLICATIONS

The present invention claims priority under 35 U.S.C. § 119 of German Application No. 196 04 583.5, filed Feb. 8, 1996, the disclosure of which is expressly incorporated by reference as if set forth in its entirety herein.

BACKGROUND OF THE INVENTION

1. Field of the Invention

This invention relates to methods of manufacturing and obtaining water-soluble proteins through recombinant DNA technology.

2. Background Information

Soluble recombinant proteins are generally produced from bacteria in such a way that a plasmid is expressed, the protein is isolated and purified. Such methods are known for the most varied proteins. For example, for expressing interferon-γ in *E. coli* the plasmid PKK 233-2 is manufactured (E. Amann and J. Brosius; Gene 40, 1985, 183 to 190). This plasmid has an inducible trc-promoter, a multiple cloning site, which contains the start codon (ATG), and terminators for the RNA polymerase.

An identical process is known from DE 40 36 856.4. In this document there is described among other things a method of producing an abbreviated interferon-γ variant (interferon-γ 10L). Here also the method proceeds from a corresponding plasmid expression. This plasmid is also expressed in bacteria cells (*E. coli*) at a rate of 30% of the total protein. In this case this interferon-y is present to over 90% in the form of insoluble, so-called "inclusion bodies". In order to purify this interferon-γ, the bacteria cells, after successful expression, are broken up, and the inclusion bodies are freed of soluble bacterial proteins by multiple washing. This breaking-up is preferably undertaken mechanically, particularly by ultrasound. The inclusion bodies are then brought into solution in a de-naturing stage, and subsequently subjected to a re-naturing stage. The renaturing stage is necessary because during manufacture of the proteins from the inclusion bodies, the protein obtained is not present in the biologically active form. The re-naturing stage is intended to cause the protein to fold into the biologically active form.

This prior art method has at least two disadvantages. First, the yield during manufacture of the proteins from the inclusion bodies is very low (e.g., in the method described above about 10%), and second, it has become apparent that the re-naturing stage does not always guarantee that the protein is always totally refolded back into its biologically active form. It has become apparent that an inhomogeneous structure population is usually present for the protein when the protein is obtained from inclusion bodies.

BRIEF DESCRIPTION OF THE DRAWING

The invention will be better understood and characteristics thereof are illustrated in the annexed drawing showing non-limiting embodiments of the invention, in which.

SUMMARY OF THE INVENTION

Figure 1:
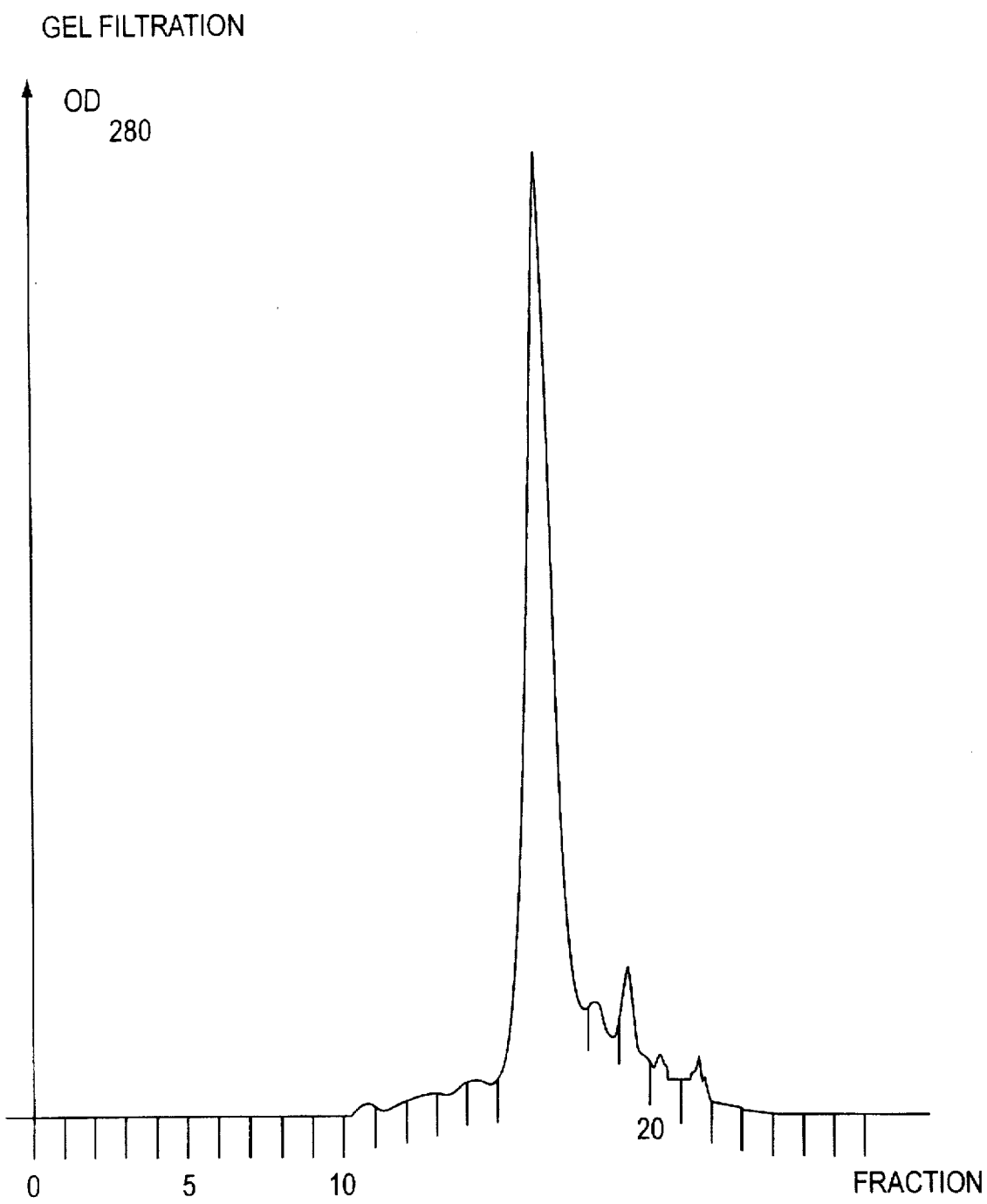
FIG. 1 illustrates the protein distribution following gel filtration.

In view of the above, there is a need for a method of obtaining recombinant proteins, such as water soluble proteins, in increased yield. There is also a need for a method of obtaining recombinant proteins with a greater proportion of the protein in active form, thus reducing or eliminating the need for refolding.

It is an object of the present invention to provide a method to obtain an increased yield of dissolved soluble proteins through recombinant DNA.

It is also an object of the present invention to provide a method that reduces the proportion of soluble proteins, obtained by recombinant DNA, contained in inclusion bodies.

It is also an object of the present invention to provide a method for obtaining soluble proteins through recombinant DNA which reduces or eliminates the need for renaturing the protein.

The present invention is directed to a method of obtaining water-soluble recombinant proteins from plasmid-containing cells. The method comprises:

a) growing a culture of cells containing a plasmid, such as bacteria, or preferably *E. coli*, to an OD 600 nm (Optical Density measured at 600 nm) of about 0.4 to 0.6, preferably to about 0.45–0.55, even more preferably to about 0.5, where the growth is preferably performed at a temperature of about 35°–38° C., even more preferably at about 37° C.;

b) cooling this culture to about 20°–26° C., more preferably to about 24°–26° C., even more preferably to about 25° C., where the cooling is done over a period of about 15–40 minutes, preferably about 25–35 minutes, even more preferably about 30 minutes;

c) inducing protein synthesis in the cooled culture by the addition of an inductor solution to achieve a final concentration of inductor, preferably IPTG, of about 10–55 µM, preferably about 10–50 µM, even more preferably about 50 µM;

d) incubating the induced culture at a temperature of about 20°–26° C., preferably about 24°–26° C., for a period of about 3.5–6.5 hours, preferably about 3.5–5.5 hours, and even more preferably at about 25° C. for about 5 hours; and e) obtaining cell pellets from the incubated culture, putting the cell pellets into a buffer, separating protein residue in the buffer from inclusion bodies and recovering the soluble recombinant protein from the protein residue.

The plasmid referred to above should contain the entire gene, preferably the complete gene for either interferon-γ or a variant of interferon-γ, behind a promoter, which is preferably a trc promoter. The soluble recombinant protein is advantageously recovered solely from the protein residue fraction. Variants of interferon-γ obtainable through this method include, for example, variants abbreviated by 10 amino acids, and/or variants which have a disulphide bridge.

DETAILED DESCRIPTION OF THE INVENTION

Surprisingly, it has become apparent that by observing the process parameters according the present invention in expression of the plasmid, it is possible to obtain the protein in a solution. After the induction phase, about 20–60% of the protein remains as soluble protein, and only the residue precipitates as inclusion bodies. In the method according to prior art, usually more than 95% of the protein is precipitated in the from of inclusion bodies. While not being bound by any one theory, it is believed that the advantage of this method resides in the fact that folding of the protein, e.g., of the interferon-γ, takes place in the spatial structure in the bacteria cell itself. Thus, with this method no de-naturing and re-naturing stages are necessary as in prior art, as the spatial structure forms in the bacteria cell itself. Incomplete refolding is therefore reduced or eliminated. A point to be particularly emphasized in this method is that by its means not only is a protein formed in the active form in a homogeneous way, but the yield from this method, e.g., for interferon-γ, is about 50%, compared to about 10% in the method of prior art.

It is important for the method according to the invention that certain method features be observed precisely. By following a combination of individual method features, it is ensured that the proteins can be obtained from the protein residue, i.e., from a protein solution. Thus, it is essential that the cell culture be raised to OD 600 nm of about 0.4 to 0.6, and that cooling then be effected in a specified defined period of time (about 15 to 40 minutes) to a specific and defined temperature (about 20° to 26° C.). This cooling, in conjunction with the extremely low inductor concentration (about 10 to 55 μM) guarantees that after an induction phase at about 20° to 26° C. of about 3.5 to 6.5 hours, about 20–60% of the protein is present in soluble form. The remainder is precipitated in inclusion bodies.

Extensive tests have shown that, for example, at temperatures of 37° C. during the induction phase, more than 95% of the protein precipitates into inclusion bodies, i.e., less than 5% remains in solution. Under the present inventive method, however, the temperature drop in conjunction with the low inductor concentration are clearly important to increasing the proportion of protein in soluble form.

Isolation and purification of the protein advantageously begin with fractionation of the culture, e.g., by centrifugation, after the expression phase. The bacteria cells are then broken up, e.g., by ultrasound, and the cell lysate is taken up with buffer. Then a protein residue and inclusion bodies can be obtained by centrifuging. Only this protein residue is used in further processing. The residue is subjected to high purification. This may be carried out for example in such a way that the protein residue is stirred with a cation exchanger material. The result is bonding of the protein to the cation exchanger. The cation exchanger material, charged with protein, can be washed with phosphate buffer and the protein can be eluted for example with saline solution in a buffer. An ammonium sulphate precipitate and gel filtration can also be connected to the high purification.

The method according to the invention is particularly suitable for manufacturing interferon-γ and its derivatives, and that, by means of this method, not only can interferon-y be obtained in the active and highly purified form described above, but also variants thereof. These include, for example, variants which are abbreviated by 10 amino acids and variants which have a disulfide bridge. Additionally, the interferon-γ and its variants may be obtained both in reduced and in oxidized form. It is until now unknown from the literature that interferon-γ can be obtained in reduced form from inclusion bodies. The method according to the invention thus is not only characterized in that proteins may be obtained in a pure form and high yield but this method clearly enables expression of proteins, such as was not possible by means of the method with the inclusion bodies.

Without limiting the invention in any way, it is believed that the advantage of this method resides in the fact that folding of the interferon-γ protein into the spatial structure takes place in the bacterial cell; there is no evidence of an inhomogeneous structure population for this protein. With the same starter, a variant of interferon-γ, which has been abbreviated by 10 amino acids, and a variant in which two cysteines have been so added that an internal disulphide bridge can form, can be synthesized and highly purified.

The yield in the purification process is up to 50% for all interferon-γ proteins investigated and is thus superior to the 10% yield for interferon-γ which is dissolved out from the inclusion bodies, and must be folded into the correct spatial structure in vitro in a reaction glass. Approximately 4 mg of highly-purified soluble interferon-γ can be obtained from 4 g of cell pellets.

The soluble interferon-γ with disulphide bridge can be purified and retained both as a reduced and as an oxidized protein. The corresponding interferon-γ from inclusion bodies can only be obtained in the oxidized form.

It is believed that interferon-γ folded in vitro is structurally inhomogeneous, whereas the soluble interferon-γ obtained by the present invention exists in a homogeneous form.

Therefore, for clinical use, the soluble interferon-γ according to the invention has no, or at least less antigen activity than the inclusion body interferon-γ.

EXAMPLE

The method according to the invention will be described in detail in the following example with reference to the manufacture of interferon-γ. As explained above, however, the method is not restricted to interferon-γ, but is basically applicable to all soluble proteins which are expressed from bacteria cells.

1. Expression (Synthesis) of Interferon-γ

E. coli cells (JM 105), with an expression plasmid which contains the complete gene for interferon-γ behind the trc-promoter, are grown to an OD 600 nm of 0.5 at 37° C. A 500 ml starter of YT medium (5 g/l yeast extract, 8 g/l Tryptone (both from Difco Laboratories, Detroit, Mich. )and 5 g/l NaCl (obtained form Merck, Darmstadt, Germany)) was started, which was inoculated with the above-mentioned culture and permitted to sit for 16 hours at 37° C. in a shaking incubator (300 rpm).

The cell culture is cooled to 25° C. over a period of 30 minutes. Synthesis of the interferon-γ is induced by the addition of 50 μM IPTG (isopropyl-S-D-thiogalactopyranoside, Sigma, Deisenhofen, Germany) final concentration. The induction phase is carried out at a temperature of 25° C. over a period of 5 hours. After this induction phase, 20 to 60% of the interferon-γ remain as a soluble protein; the remainder of the interferon-γ is precipitated in the form of inclusion bodies.

2. Fractionation of the Interferonγ

After the five hour expression phase the bacteria cells are collected by centrifuging (15 minutes; 6000 rpm in a JA 15 rotor) to form cell pellets. The cells are resuspended and washed in 200 ml Phosphate Buffered Saline (PBS) buffer (20 mM sodium phosphate (pH=7.4) and 150 mM NaCl, both from Merck, Darmstadt, Germany) or Na-phosphate buffer (20 mM (pH 7.0), Merck, Darmstadt). By means of renewed centrifuging, as above, a washed cell pellet is obtained which is either immediately purified or is stored at −70° C.

The washed cell pellet is taken up in 15 ml PBS or Na-phosphate buffer and the cells are opened by 5 ultrasound treatments of 10 seconds each (5×10 seconds) with cooling on ice. 15 ml buffer are added to the cell lysate, and the diluted cell lysate is fractionated by centrifuging (30 minutes; 10000 rpm; 7A 20 rotor) to form a soluble protein residue (fraction I) and a cell lysate pellet which contains the inclusion bodies.

3. High Purification of the Soluble Interferon-γ SP-Sepharose 1 ml of an SP-Sepharose (Pharmacia, Uppsala, Sweden) balanced in the same buffer are stirred carefully into fraction I (with a cation bond of 20 mg protein). After 30 minutes on ice, centrifuging is carried out for 10 minutes at 3500 rpm. The SP-Sepharose pellet to which the interferon-γ is bound, is freed of *E. coli* proteins in two successive washing stages each with 15 ml buffer. The bonded interferon-γ is eluted with 2 ml 1M NaCl entirely in the buffer and separated by centrifuging from the SP-Sepharose material. The elution steps are repeated twice until it is certain that all interferonγ has been eluted from the SP-Sepharose material. Elution of the protein was monitored by an OD 280/260 nm measurement. Both fractions with the highest OD, normally the two first eluates, are purified to form fraction II. This purification stage is extremely efficient due to the high isoelectric point (IP) of interferonγ, which is more than 10. In this batch process, the purity of the interferon-γ is increased from about 5% to more than 90%.

Ammonium Sulphate Filling

Fraction II (4 ml) is brought to an AS (pulverized ammonium sulphate, Merck, Darmstadt, Germany) saturation of 70% by the slow addition of 440 mg of finely pulverized AS. After about 12 hours at 4° C., the precipitated interferonγ is collected as an AS pellet by centrifuging (30 minutes at 10000 rpm; JA 20 rotor). The pellet is taken up in 1 ml buffer (fraction III).

Gel Filtration 1 ml of fraction III is aseptically filtered (0.2 μM pore size) and fractionated in different sample sizes (200 μl -1 ml) with the aid of a TSKG 200 column (Pharmacia/LKB, Uppsala, Sweden). This gel filtration stage (FIG. 1) gives a symmetrical distribution of the interferon-γ protein and indicates with the aid of calibration proteins that the interferon-γ is present as a homodimeric protein.

4. Characterization of Soluble Interferon-γ

An SDS gel (sodium dodecylsulphate) electrophoresic analysis gives a degree of purity of more than 95%. Although in direct comparison with the corresponding interferonγ from inclusion bodies, a slightly more rapid migration behavior is observed, which indicates a minimum abbreviation by a few amino acids, the soluble interferon-γ can be obtained by this procedure as a completely intact protein. The antiviral activity was measured in U/mg. The international WHO standard Gxg01-902-535 was calibrated against the recombinant interferon-γ variants in the laboratory. One unit of interferon-γ protects half of the A549 cells infected with the EMC virus from the cytopathic effect of the virus. The specific antiviral activity of the soluble interferon-γ with $2- \times 10^7$ U/mg protein corresponds to that of the interferon-γ from inclusion bodies.

It is noted that the foregoing example has been provided merely for the purpose of explanation and in no way is to be construed as limiting of the present invention. While the invention has been described with reference to a preferred embodiment, it is to be understood that the words which have been used herein are words of description and illustration, rather than words of limitation. Changes may be made, within the purview of the appended claims, as presently stated and amended, without departing from the scope and spirit of the invention in its aspects. Although the invention has been described herein with reference to particular means, materials and embodiments, the invention is not intended to be limited to the particulars disclosed herein; rather, the invention extends to all equivalents such as are within the scope of the appended claims as presently stated.

We claim:

1. A method of obtaining soluble recombinant protein from plasmid-containing bacteria comprising:
    a) growing a culture of bacteria containing a plasmid at a temperature of about 35–38 degrees C., in which the plasmid contains a entire gene behind a promoter, to an OD 600 nm of about 0.4 to 0.6;
    b) cooling said culture to a temperature of about 20°–26° C. for a period of about 15–40 minutes to obtain a cooled culture;
    c) inducing protein synthesis in said cooled culture by the addition of an inductor solution to obtain a final inductor concentration of about 10–55 μM, to obtain an induced culture;
    d) incubating said induced culture at a temperature of about 20°–26° C. for a period of about 3.5–6.5 hours to obtain a final culture; and
    e) obtaining cell pellets from said final culture, putting said cell pellets into a buffer, separating protein residue in said buffer from inclusion bodies and recovering said soluble recombinant protein from said protein residue.

2. The method of claim 1 wherein said period of said incubation is about 3.5–4.5 hours.

3. The method of claim 1 wherein said inductor is IPTG.

4. The method of claim 1 wherein said plasmid contains the complete gene for interferonγ.

5. The method of claim 1 wherein said promoter is a trc promoter.

6. The method of claim 1 wherein said growing is done to an OD 600 nm of about 0.45–0.55.

7. The method of claim 6 wherein said growing is done to an OD 600 nm of about 0.5.

8. The method of claim 1 wherein said cooling is to about 24°–26° C.

9. The method of claim 8 wherein said period of said incubation is about 3.5–5.5 hours.

10. The method of claim 8 wherein said cooling is to about 25° C.

11. The method of claim 1 wherein said period of said cooling is about 25–35 minutes.

12. The method of claim 11 wherein said period of said cooling is about 30 minutes.

13. The method of claim 1 wherein said final inductor concentration is about 10–50 μM.

14. The method of claim 13 wherein said final inductor concentration is about 50 μM.

15. The method of claim 1 wherein said temperature of said incubating is about 24°–26° C.

16. The method of claim 15 wherein said period of said incubation is about 3.5–5.5 hours.

17. The method of claim 15 wherein said growing is done to an OD 600 nm of about 0.45–0.55, said cooling is to about 24°–26°C, said period of said cooling is about 25–35 minutes, and said final inductor concentration is about 10–50 μM.

18. The method of claim 17 wherein said temperature of said incubating is about 25° C. and said period of said incubating is about 5 hours.

19. The method of claim 15 wherein said growing is done to an OD 600 nm of about 0.5, said cooling is to about 24°–26°C., said period of said cooling is about 30 minutes, and said final inductor concentration is about 50 μM.

20. The method of claim 19 wherein said period of said incubation is about 3.5–5.5 hours.

21. The method of claim 19 wherein said temperature of said incubating is about 25° C. and said period of said incubating is about 5 hours.

22. The method of claim 21 wherein said bacteria comprise *E. coli*, said growing is at about 37° C., said promoter is a trc promoter, said cooling is to about 25° C., said inductor is IPTG, said plasmid contains the complete gene for interferon-γ, and said obtaining is done by centrifuging.

23. The method of claim 15 wherein said temperature of said incubating is about 25° C. and said period of said incubating is about 5 hours.

24. The method of claim 23 wherein said plasmid contains the complete gene for interferon-γ.

25. The method of claim 1 wherein said growing is done at a temperature of about 37° C.

26. The method of claim 19 wherein said period of said incubation is about 3.5–5.5 hours.

27. The method of claim 1 wherein said bacteria comprise *E. coli*.

28. The method of claim 27 wherein said bacteria consists of *E. coli*.

* * * * *